US008455442B2

(12) United States Patent
Kunze et al.

(10) Patent No.: US 8,455,442 B2
(45) Date of Patent: Jun. 4, 2013

(54) PEPTIDES HAVING BINDING AFFINITY TO AN ANTIBODY WHICH RECOGNIZES AN EPITOPE ON AN α1 LOOP 2 OR β2 LOOP 1 OF AN ADRENORECEPTOR

(75) Inventors: Rudolf Kunze, Berlin (DE); Gerd Wallukat, Berlin (DE); Peter Rosenthal, Lüdenscheid (DE); Richard Straube, Lüdenscheld (DE)

(73) Assignees: MDC Max-Delbruck-Centrum fur Molekulare Medizin Berlin-Buch, Berlin-Buch (DE); Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/735,416

(22) PCT Filed: Jan. 15, 2009

(86) PCT No.: PCT/EP2009/050446
§ 371 (c)(1),
(2), (4) Date: Oct. 27, 2010

(87) PCT Pub. No.: WO2009/090227
PCT Pub. Date: Jul. 23, 2009

(65) Prior Publication Data

US 2011/0104226 A1 May 5, 2011

(30) Foreign Application Priority Data
Jan. 15, 2008 (EP) .................................... 08100510

(51) Int. Cl.

| | |
|---|---|
| *A61K 38/03* | (2006.01) |
| *A61K 38/04* | (2006.01) |
| *A61K 38/08* | (2006.01) |
| *C07K 4/12* | (2006.01) |
| *C07K 7/06* | (2006.01) |
| *C07K 17/00* | (2006.01) |

(52) U.S. Cl.
USPC ............ 514/16.4; 514/1.1; 530/300; 530/329

(58) Field of Classification Search
None
See application file for complete search history.

(56) References Cited

FOREIGN PATENT DOCUMENTS

| | | |
|---|---|---|
| EP | 1 832 600 | 9/2007 |
| WO | WO 02/38592 | 5/2002 |
| WO | WO 02/088706 | 11/2002 |
| WO | WO 02/093174 | 11/2002 |
| WO | WO 2006113602 A2 * | 10/2006 |
| WO | WO 2008/151847 | 12/2008 |

OTHER PUBLICATIONS

Fu MLX et al. Characterization of anti-peptide antibodies directed against an extracellular immunogenic epitope on the human alpha1-adrenergic receptor. Clin. Exp. Immunol. 97:146-151 (1994).*

Fu MLX et al. Functional autoimmune epitope on alpha1-adrenergic receptors in patients with malignant hypertension. Lancet, 344(8938):1660-1663 (1994).*

Walsh, "The role of cell derived oligomers of A[beta} in Alzheimer's disease and avenues for therapeutic intervention." Biochemical Society Transactions, vol. 33, No. 5, Nov. 2005, pp. 1087-1090.

Selkoe et al. "Alzheimer's disease: molecular understanding predicts amyloid-based therapeutics." Annual Review of Pharmacology and Toxicology, vol. 43, 2003, pp. 545-584.

Selkoe et al. "Defining molecular targets to prevent Alzheimer disease." Archives of Neurology, vol. 62, No. 2, Feb. 2005, pp. 192-195.

Terryberry et al. "Autoantibodies in neurodegenerative diseases: antigen-specific frequencies and intrathecal analysis." Neurobiology of Aging, vol. 19, No. 3, Jan. 1, 1998, pp. 205-216.

Lazarov et al. "Electron microscopic structure of purified, active gamma-secretase reveals an aqueous intramembrane chamber and two pores." Proceedings of the National Academy of Sciences of the United States of America, vol. 103, No. 18, May 2, 2006, pp. 6889-6894.

Sunaga et al. "Glyceraldehyde-3-phosphate dehydrogenase is overexpressed during apoptotic death of neuronal cultures and is recognized by a monoclonal antibody against amyloid plaques from Alzheimer's brain." Neuroscience Letters, vol. 200, No. 2, Oct. 1, 1995, pp. 133-136.

Elies et al. "Structural and functional analysis of the B cell epitopes recognized by anti-receptor autoantibodies in patients with Chagas'Disease." Journal of Immunology, American Association of Immunologists, vol. 157, No. 9, Jan. 1, 1996, pp. 4203-4211.

Eng et al. "Beta2-Adrenergic receptor antibodies in *Myasthenia gravis*." Journal of Autoimmunity, vol. 5, No. 2, Apr. 1, 1992, pp. 213-227.

Tate et al. "Epitope analysis of T- and B-cell response against the human betal-adrenoceptor." Biochimie, vol. 76, No. 2, Jan. 1, 1994, pp. 159-164.

Magnusson et al. "Antigenic analysis of the second extra-cellular loop of the human beta-adrenergic receptors." Clinical and Experimental Immunology, vol. 78, No. 1, Oct. 1, 1989, pp. 42-48.

Ni et al. "Activation of beta2-adrenergic receptor stimulates gamma-secretase activity and accelerates amyloid plaque formation." Nature Medicine, vol. 12, No. 12, Dec. 2006, pp. 1390-1396.

* cited by examiner

*Primary Examiner* — Elizabeth C Kemmerer
*Assistant Examiner* — Kimberly A Ballard
(74) *Attorney, Agent, or Firm* — Jacobson Holman PLLC (57) ABSTRACT

A peptide having an $ED_{50}$ of less than 500 nm, in particular 10 nM to an antibody which recognizes an epitope on an extracellular α1 loop 2 or β2 loop 1 of a human adrenoceptor wherein the antibody's binding to the epitope results in an increase of γ-secretase activity, an increased release of β-amyolid molecules and/or cellular dysfunction of cerebral blood vessel cells, glia cells or neurons, wherein the $ED_{50}$ value is measured by bioassay.

7 Claims, 2 Drawing Sheets

PEPTIDES HAVING BINDING AFFINITY TO AN ANTIBODY WHICH RECOGNIZES AN EPITOPE ON AN α1 LOOP 2 OR β2 LOOP 1 OF AN ADRENORECEPTOR

This is a national stage of PCT/EP09/050446 filed Jan. 15, 2009 and published in English, which has a priority of European no. 08100510.0 filed Jan. 15, 2008, hereby incorporated by reference.

The invention pertains to a peptide having a binding affinity an antibody which recognizes an epitope on an α1 loop 2 or β2 loop1 of an adrenoreceptor, an isolated nucleic acid molecule, solid phases for affinity chromatography or solid-phase extraction consisting of organic, inorganic, synthetic polymers or of mixed polymers, a vector comprising a nucleic acid molecule, a host cell comprising the vector, a device for removing immunoglobulins from immunoglobulin-containing fluids on solid phases, a pharmaceutical composition comprising a nucleic acid molecule, a peptide and/or a solid phase of the invention together with a pharmaceutically tolerable carrier, a kit comprising a nucleic acid molecule of the invention, a vector of the invention, a host cell of the invention, as well as an apparatus for chromatography, comprising peptides of the invention.

Alzheimer's disease (AD), which is named after its discoverer Alois Alzheimer (1864-1915), is a progressive degenerative disease. It is characterized by changes in the cerebral cellular structure and function caused by deposits of aggregated proteins with extensive consequences for essential brain functions. The following clinical and cognitive characteristics are essential:

disorders of the short-term memory at first and of the long-term memory later on disorders of the perception of simple recognition patterns progressive loss of speech and articulateness progressive loss of sense of smell, of spatial orientation and decline of ability to perform routine tasks.

The diagnosis "AD" is obtained by different methods, for example, with imaging methods, such as computer tomography (CT) or magnetic resonance tomography (MRT) and by the chemical determination in the laboratory of the concentrations of the involved pathological molecules in the cerebrospinal fluid. Electroencephalography (EEG) may also be recurred to. Cognitive tests, such as the mini mental status test (MMST) are increasingly gaining importance.

If untreated, the disease is a "one-way street" which unavoidably results in a deterioration of the clinical image over several years to end with death. The more advanced the stage of the disease, the more care and cost intensive the patient becomes. This also holds for other forms of dementia (AD accounting for about two thirds of all dementia cases), which will not be dealt with here, however.

The prevalence of the disease is highly age-dependent. Among those of 60 to 70 years of age, it is about 1%, and among those of 70 to 80 years of age, it is as high as about 10%. Since life expectancy of the humans in Germany is continuously increasing, another rise of the number of cases is to be expected.

Currently, the annual incidence for AD in Germany is 130 000 to 140 000 incidences (Hallauer, 2003), a number that needs interpretation, however. Since the mild form is little conspicuous, the majority of the patients will probably have a medium severity of the disease.

Some years ago, the disease was still considered a stroke of fate that could not be cured. Severe cases have been treated with sedatives and neuroleptics for sedation. In the meantime, drugs of the first generation are available; they are mainly employed in the medium, moderate stage. Examples include approved pharmaceuticals, such as Axura (active ingredient: memantine) or Exelone (active ingredient: rivastagmine). According to the published state of the study, these agents have a good effectiveness for mild and medium severities of AD.

However, the clinical effectiveness of Exelone and other choline-esterase inhibitors is denied according to metaanalyses. Although approved medicaments are available on the market and the preparations are prescribable, by far not all patients are treated.

Some prophylactic effect on AD seems to be exerted by anti-inflammatory drugs, such as acetylsalicylic acid (aspirin), ibuprofen, indomethazine or COX2 inhibitors. Evidently, local and systemic inflammations or inflammation mediators play a disease-promoting role in the organism/brain, probably due to an acceleration of neurofibril formation.

Cholesterol-reducing agents, such as statins, also seem to have a favorable influence on the risk of developing AD. At least, patients obtaining cholesterol-reducing agents exhibit a lesser incidence of AD. However, no hard scientific data are available to support this.

The situation is similar with hypotensive agents, such as inhibitors of angiotensin converting enzyme (ACE). In addition to a direct effect of these active substances, the reduction of the systolic blood pressure is also generally associated with the preventive effects observed.

Immunizations of patients with β-amyloid are in the experimental stage of a therapy. In response, the immune system produces antibodies which then destroy amyloid plaques by a local inflammatory reaction. This approach seems to be promising, but is not undisputed, because it involves high risks. Probably, the individual inflammatory immune responses that are used therapeutically cannot be dosed as precisely as would be required. Other experimental-therapeutic approaches are based on the compensation of a cerebral deficiency of copper ions, which evidently plays a role in plaque formation.

The question of whether medicaments are basically able to achieve a standstill only, or also a clinical improvement of the patients' cognitive state is currently still unanswered. The currently available means stabilize the clinical picture rather than improve it.

The pathogenesis of AD itself has not yet been finally clarified. A number of risk factors have been recognized. These include age, hypertension, high cholesterol levels, overweight, apolipoprotein E4, copper deficiency, certain genetic predispositions, and possibly oxidative stress. The development of the disease is very probably multifactorial.

There is a plethora of references about molecules that play or could play a role in the development and progress of AD. As to a definition of term, it may be mentioned here that most of the so-called pathological molecules are components of physiological structures and processes in the healthy organism. They are considered pathological if they exceed concentration limits, in the plasma or locally in the tissue, intercellular or intracellular. This holds for both dissolved proteins and aggregated molecules (e.g., β-amyloid in the form of plaque).

The aggregation or deposit of two different, per se physiological protein molecules in the brain in intercellular or intracellular spaces causes fundamental neuronal functional disorders in signal transmission and the interaction of neurons. These proteins are essentially the neurotoxic β-amyloid peptide (aggregated as a polymer in the form of amyloid plaque), and the Tau protein, a polymer aggregated as neurofibrillary tangles.

induce the beginnings of the disease and promote its development and maintenance. Table 1 provides a survey of important pathological molecules.

TABLE 1

Survey of pathological molecules of Alzheimer's disease in the blood plasma

| Pathological molecules in AD | MW | Comment |
| --- | --- | --- |
| fragments of β-amyloid | <4,000 | fragments of β-amyloid having |
| oligomers of β-amyloid | >4,000 | neurotoxic properties |
| β-amyloid or fragments thereof bound to albumin | >70,000 | albumin is the most important plasma protein for the physiological clearance of noxious substances |
| apolipoprotein E, especially E4 | ca. 34,000 (monomer) | predisposed for AD, may be contained in plaques |
| proinflammatory cytokines IL1β, IL6, TNFα | 16,000-50,000 (monomer and trimer, respectively | increased levels in brain, neurotoxic |
| C-reactive protein (CRP) | 120,000 | involved in plaque formation, enhances cell degradation in necroses |
| fibrinogen | 340,000 | rheologically effective due to its size, reduces circulation through capillaries |
| L-kynurenine | 208 | neurotoxic precursor of 3OH—K, interacts with glutamate receptors |
| homocysteine, unbound | 268 | inhibits the degradation of ADMA and thus reduces vasodilatation |
| asymmetric dimethylarginine (ADMA) | 202 | inhibits NO synthetase and thus results in hypoperfusion |
| oxidative stress (reaction products) | variable, also microparticles | can be induced directly by β-amyloid, but are also formed by hypoperfusion |

So-called amyloids are evidently involved causally in the development of AD. Thereafter, an increased formation of amyloid-β40/42 occurs by enzymatic cleavage of the molecule from the membrane of the nerve cells. This results in a locally increased concentration of single β-amyloid molecules, β-amyloid oligomers and its aggregation into amyloid plaques. These plaques disrupt the normal transmission of stimuli by the nerves and communication between the cells. The cleavage of aggregatable β-amyloids from the precursor molecules is effected by the so-called γ-secretase. The activity of this enzyme is controlled by the β2-adrenoceptor.

The plaques in turn may also result in the generation of neurofibrillary tangles of the Tau protein, which normally is physiologically localized in the axonal tracts of the nerve cells. The deposit of these aggregates takes place in a wide variety of cerebral areas. The process of plaque formation proceeds over many years from the beginning to the onset of the disease.

Both plaques and neurofibrillary tangles can be visualized well by microscopy in brain sections of dead AD patients and are an important part of diagnostics.

A pathomechanistic role of other molecules is also discussed in parallel, including the role of apolipoprotein E4. Further, rheologically relevant plasma proteins seem to be involved in the development of the clinical picture at least indirectly. These include increased or moderately increased systemic levels and local concentrations of alpha-2 macroglobulin, fibrinogen, but also oxidized plasma proteins from oxidative stress reactions, such as oxidized low density lipoprotein (oxLDL).

The sum of effects of these molecules may contribute to a reduced blood circulation through the brain areas and thus The most extensively studied group of diseases associated with agAAB against GPCR are cardiac diseases. In myocarditis, dilated cardiomyopathy, peripartum cardiomyopathy, Chagas' disease, and ventricular arrhythmias, agAAB against the $\beta_1$-AR can be detected in the sera of patients with clinically diagnosed diseases.

DCM and myocarditis are severe heart disorders, and it has been hypothesized that a chronic myocarditis may develop to a DCM. In both diseases an infection with an enterovirus or others may be the primary etiological agent, but the inflammatory response may have developed to an autoimmune disease. In a later stage, the infectious agent may not be detectable, and even the inflammatory response may have declined, however, a chronic progressing heart failure is diagnosed. The DCM is characterized by a severe heart failure. In a subset of DCM, the idiopathic DCM, in which other etiological agents can be excluded, the prevalence of the $\beta_1$-adrenergic AAB of up to 80% is remarkable.

Myocarditis and DCM are preferentially treated by antagonists of the β1-adrenergic and renin-angiotensin system and physical rest.

The therapeutic goal is to reduce cardiac overstimulation and prevent arrhythmias The therapeutic use of betablockers in reducing adrenergic overstimulation is accompanied by a significant decrease in cardiac death and hospitalization in the patients subject to the study. Ventricular arrhythmias are a major cause of sudden death in dilated DCM and ventricular tachycardias have been shown to be strongly related with the detection of agAAB to the $\beta_1$-AR.

The chronic progression of heart failure in DCM leads to a stage of the disease where successful medication is not possible anymore. In this stage, only heart transplantation can be considered as a therapy sustainable for some year. DCM is the cause of about half of the heart transplantations. An extension of therapeutic options might very likely prevent a substantial number of premature deaths in the case of severe heart failure.

Similar to DCM, peripartum cardiomyopathy is characterised by a dilation of the left ventricle and may develop into a life threatening disorder. The incidence is about 1:1000 in South African women, while the disease is rare among white populations in western countries. The etiology of peripartum cardiomyopathy is largely unknown. By definition it is diagnosed between the last month before and the $4^{th}$ month after delivery. Recently, the presence of agAAB against the $\beta_1$-AR in all sera of a sample of 10 patients suffering from peripartum cardiomyopathy was shown.

Chagas' disease is caused by the parasite *Trypanosoma cruzi* and very common in South America. Among other symptoms, the patients often develop a myocarditis as part of the dysautonomic syndrome that affects the whole cholinergic system. There is strong evidence that the dysautonomic syndrome is caused also by functional AAB against the muscarinic $M_2$-acetylcholine receptor. The prevalence of agAAB against the $M_2$-receptor ranges from 50-94%. In Chagas' disease, AAB against the $\beta_1$-AR can also be found in about 53% of the cases. This situation may represent the antigenic mimicry of originally the same antigen from *T. cruzi*, with a functional antagonism as an epiphenomenon.

With respect to the pathogenetic nature of the described agAAB, only the signalling events with evidence of clinical relevance will be considered in the following paragraph. Activation of the $\beta$-AR leads to an elevation of cAMP by the activation of adenylate cyclase by stimulating $G_s$-proteins in the G-protein trimer. On the other hand, agonistic ligand binding to muscarinic and nicotinic acetylcholine receptors inhibits adenylate cyclase by inhibiting $G_i$-proteins. However, this simple pattern has to be extended for the individual receptors.

Autoantibodies from sera of myocarditis or DCM patients show a positive chronotropic effect to the same extent as the agonist isoprenaline. Isoprenaline clearly increases the cAMP concentration in the cell and activates the L-type $Ca^{2+}$-channels. It has been shown that AAB from DCM patients activate the L-type $Ca^{2+}$-channels. On the other hand, the effect of AAB on the accumulation of cAMP was rather marginal. It has been shown, however, that the cytosolic as well as the membrane bound protein kinase A in cardiomyocytes is activated upon AAB-stimulation. A monoclonal anti-$\beta_1$-receptor AB that induces apoptosis in rat cardiomyocytes also acts via cAMP and protein kinase A, MAP-kinases, esp. p38-kinase are activated downstream of several GPCRs but also in the signal transduction cascade of inflammatory cytokines. Thus, it may be suggested that stimulation of the $\beta_1$-AR by agAAB may also have a proinflammatory effect.

There are also important cAMP-independent signalling pathways. L-type $Ca^{2+}$-channels are not only activated through phosphorylation by protein kinase A, but also directly through subunits of G-proteins. Thus, the stimulation of $Ca^{2+}$-influx may be a significant pathway for the pathogenetic role of AAB in autoimmune myocarditis and DCM. The action potential on rat and human cardiomyocytes is prolonged by the administration of agAAB against the $\beta_1$-AR and activates in turn the electrogenic $Na^+/Ca^{2+}$-exchanger, resulting in electrical instability of the heart. Intracellular calcium overload is also known as a key event of remodelling, as is the $\beta_1$-adrenergic stimulation. In a transgenic rat model, the $\beta_1$-AR was crucial for the reorganization of actin mediated by enhanced transcription of the atrial natriuretic factor.

Taken altogether, $\beta$-adrenergic overstimulation, intracellular calcium overload, and the partial lack of down regulation of the $\beta_1$-AR may be involved in the pathogenesis of myocarditis and DCM.

Results from animal experiments support the in vitro data about the pathogenic relevance of agAAB obtained in tissue culture experiments. Jahns et al. could induce agonistic antibodies in rats by immunisation with the second extracellular loop of the $\beta_1$-AR. The animals developed a dilated cardiomyopathy similar to that of human dilated cardiomyopathy. The transfer of the induced antibody/immunoglobobulins into healthy animals leads to a DCM also.

The induction of agonistic antibody against the $\beta_1$-AR was also performed in rabbits and results in the occurrence of agAAB as well as DCM. A removal of agAAB from the animals blood plasma by specific immunoadsorption using a peptid column leads to an improvement of the heart muscle function, measured as left ventricular ejection fraction.

More as a dozen publications report about the the clinical benefit of the theapeutical apheresis (immunoadsorption) in patients suffering from DCM. In a clinical stage of the cardiac disease where no successful cardiac drug medication is possible, the therapeutical apheresis leads to a long lasting decline of the agAAB, a disappearance of activated inflammatory leukocytes from the heart muscle tissue and an increase of essential cardiac functions.

Other examples of diseases which are associated or caused by agAAB preeclampsia and vascular necrotic kidney rejection (agAAB against the Angiotensin-1 receptor or the open angle glaucoma (agAAB against the $\beta$2-adrenoceptor.

WO-A-02/093174 discloses a method and device for treating AD. The method involves the removal of circulating autoantibodies of a biochemical marker of markers, specifically human glial fibrillary acidic protein (GFAP) and glyceraldehyde-3-phosphate dehydrogenase (GAPDH), in body fluid, preferably blood or a blood product. The invention further includes a device or process of immune system modulation effective for autoantibody removal.

D. M. Walsh et al. discloses in Biochemical Society Transactions (2005) Vol. 33, part 5, PP 1087-1090 that soluble oligomers of A$\beta$ are among the earliest effectors of Alzheimer's disease. They report about testing of compounds directed at three prominent amyloid-based therapeutic targets, inhibition of the secretases responsible for A$\beta$ production, inhibition of A$\beta$ aggregation and immunization against A$\beta$. In each case, compounds capable of reducing oligomer production or antibodies that avidly bind A$\beta$ oligomers also ameliorate the synaptotoxic effects of these natural, cell-derived oligomers.

Norman R. Relkin et al. discloses in Neurobiology of Aging 2008 Feb. 20, E-publ. that natural occurring antibodies against $\beta$A are able to reduce the $\beta$A level in the body, and their intravenious application may improve the brain function in patients with mild AD.

Dennis J. Selkoe et al. Report in Annu. Rev. Pharmacol. Toxicol. 2003, 43:545-84 discusses molecular understanding predicting amyloid-based therapeutics. Degenerative diseases of the brain were long considered among the most obscure and intractable of human maladies. However, recent advances in understanding their mechanisms have brought us to the verge of potential disease-modyfying agents. This progress is perhaps best exemplified by the case of Alzheimer's disease. The application of molecular pathology and genetics has led to the recognition that the four genes implicated to date in familial Alzheimer's disease all chronically elevate cerebral levels of the Amyloid $\beta$-protein (A$\beta$). Accordingly, small molecule inhibitors of the $\beta$- and $\gamma$-secretases, the proteases that generate Aβ from its precursor, are under actice development, and some have shown in vivo efficacy in mouse models. An alternative approach, active or passive immunization against Aβ, has received extensive pre-clinical validation in mice, but an effective preparation free of significant side effects in humans is still awaited. Several other potential therapies are also reviewed here. If one or more of these varied approaches is ultimately proven to slow or prevent dementia, Alzheimer's disease will become a salient example of the successful application of reductionist biology to the most complex of organs, the human cerebral cortex.

EP-A-1832600 discloses an invention which relates to nucleic acid molecules encoding peptides which interact with autoantibodies associated with glaucoma, to the peptides themselves, to a pharmaceutical composition comprising said nucleic acid molecules and peptides, and to the use of said peptides—especially in apheresis—for the treatment of glaucoma. The peptides represent an epitope which is a part of the extrcallular loop2 of the β2 adrenergic receptor.

WO-A-02/38592 discloses an invention which relates to peptides having a high affinity to immunoglobulins.

Y. Magnusson et al. report in Clin. Exp. Immunol. (1989) 78, 42-48 about an antigenic analysis of the second extracellular loop of the human beta-1 adrenergic receptor which is different to the beta-2 adrendergic receptor.

Yanxiang Ni et al. report about activation of $β_2$-adrenergic receptor stimulating γ-secretase activity and accelerating amyloid plaque formation. They report that $β_2$-AR activation can stimulate γ-secretase activity and amyloid plaque formation and speculates that abnormal activation of $β_2$-AR might contribute to Aβ accumulation in Alzheimer's disease pathogenesis.

An object of the invention was to provide a compound which is able to be used in the treatment of AD. Another object was to provide a compound which is able to reduce the β2-adrenoceptor mediated γ-secretase activity in individuals suffering from higher levels of γ-secretase due to auto-antibodies against adrenoreceptor.

The invention is based on the finding of agonistic autoantibodies (agAAB) directed against the G protein coupled receptors (GPCR), β2 and α1 adrenoceptor (AR), in the blood plasma of patients suffering from diseases caused by an increase of γ-secretase activity, an increased release of β-amyolid molecules and/or cellular dysfunction of cerebral blood vessel cells, glia cells or neurons. In particular, the disease is AD.

In one embodiment of the present invention the object is solved by removing immunoglobulins from patients being suspect of suffering from or suffering from a disease caused by an increase of γ-secretase activity, an increased release of β-amyolid molecules and/or cellular dysfunction of cerebral blood vessel cells, glia cells or neurons. The removal of immunoglobulins may be performed by adsorption of the respective immunoglobulins on a solid support. These methods as such are well known in the art.

In a further embodiment the invention is concerned with the use of an immunoadsorption device for manufacturing a device for the treatment of a disease caused by an increase of γ-secretase activity, an increased release of β-amyolid molecules and/or cellular dysfunction of cerebral blood vessel cells, glia cells or neurons by removal of immunoglobulins from patients.

In another embodiment of the invention the object is solved by a peptide having an $ED_{50}$ of less than 500 nM, in particular 10 nM to an antibody which recognizes an epitope on a human α1 loop 2 and β2 loop1 of an adrenoreceptor wherein the antibody's binding to the epitope results in increase of rsecretase activity and/or increased pathological β-amyloid release and/or cellular dysfunction of cerebral blood vessel cells, glia cells or neurons, wherein the $ED_{50}$ value is measured by the bioassay which was used to identify the agAAB.

In particular, the peptide of the invention recognizes the human α1 loop epitopes of α-adrenoreceptor subtypes A, B, or C or combinations thereof.

In one embodiment of the invention the peptide of the invention consists of an amino acid sequence

X1-X2-X3-X4-X5-X6-X7-X8-X9 wherein
a)
X1=amino group, amide, acetyl group, biotin group, marker, spacer, linker, C, GKK, SGKK (SEQ ID NO: 6) or deletion,
X2=A, G, α-Abu, F, Hph, Hyp, Nal, P, Pip, S, V, W, Y, or deletion,
X3=Hyp, P, Pip, S, T, Y, or deletion,
X4=Aad, Asu, D, E, Har, K, N, Orn, Q, R,
X5=Aad, Asu, D, E, N, Q,
X6=Aad, Asu, D, E, Har, K, N, Orn, Q, R,
X7=F, Hph, Hyp, Nal, P, Pip, W, Y, or deletion,
X8=A, α-Abu, β-A, G, S, T, V, Y, or deletion,
X9=amide, hydrazide, azide, carbamate, marker, spacer, linker, C, GKK, SGKK (SEQ ID NO: 6) or deletion, or
b)
X1=amino group, amide, acetyl group, biotin group, marker, spacer, linker, C, GKK, SGKK (SEQ ID NO: 6) or deletion,
X2=F, Hph, Hyp, Nal, P, Pip, W, Y,
X3=A, α-Abu, Dab, G, Hyl, K, Orn, R, S, V,
X4=Aad, Asu, D, E, Hyp, N, P, Pip, Q,
X5=Aad, Asu, D, E, Hyp, N, P, Pip, Q,
X6=A, α-Abu, G, Hyl, K, Orn, R, S, V
X7=F, Hph, Hyp, Nal, P, Pip, W, Y,
X8=γ-Abu, Ahx, β-A, G, or deletion,
X9=amide, hydrazide, azide, carbamate, marker, spacer, linker, C, GKK, SGKK (SEQ ID NO: 6) or deletion, or
c)
X1=amino group, amide, acetyl group, biotin group, marker, spacer, linker, C, GKK, SGKK (SEQ ID NO: 6) or deletion,
X2=A, α-Abu, Dab, G, Hyl, K, Orn, R, or deletion,
X3=A, C, F, Hph, M, Nal, S, W, Y,
X4=F, S, T, W, Y,
X5=F, S, T, W, Y,
X6=A, C, F, Hph, M, Nal, S, W, Y,
X7=A, α-Abu, Dab, G, Hyl, K, Orn, R,
X8=Abu, Ahx, β-A, G, or deletion,
X9=amide, hydrazide, azide, carbamate, marker, spacer, linker, C, GKK, SGKK(SEQ ID NO: 6) or deletion, or
d)
X1=amino group, amide, acetyl group, biotin group, marker, spacer, linker, C, GKK, SGKK (SEQ ID NO: 6) or deletion,
X2=Aad, Asu, D, E, F, Hph, N, Nal, Q, W, Y,
X3=A, C, G, Hcy, S, Sec,
X4=D, E, F, N, Nal, Q, W, Y,
X5=F, Hph, Nal, W, Y,
X6=D, E, F, N, Nal, Q, W, Y,
X7=A, C, G, Hcy, S, Sec,
X8=Aad, Asu, D, E, F, Hph, N, Nal, Q, W, Y,
X9=amide, hydrazide, azide, carbamate, marker, spacer, linker, C, GKK, SGKK (SEQ ID NO: 6) or deletion wherein Aad is α-aminoadipic acid; α-Abu is α-aminobutyric acid; Ahx is ε-aminohexanoic acid; Asu is α-aminosuberic acid; β-A is β-Alanine; Dab is α,γ-diaminobutyric acid; γ-Abu is γ-aminobutyric acid; Har is homoarginine; Hcy is homocysteine; Hph is homophenylalanine; Hyl is δ-hydoxylysine; Hyp is hydroxyproline; Nal is β-(1- or 2-naphthyl)-alanine; Orn is ornithine; Pip is pipecolic acid; Sec is selenocysteine and the single letter code of amino acids represents the common L-amino acids according IUPAC nomenclature as well as the corresponding D-amino acids.

In a further embodiment of the invention the peptide according the invention is characterized in that the linker and/or a spacer are selected from the group consisting of α-aminocarboxylic acids as well as homo- and heterooligomers thereof, α,ω-aminocarboxylic acids and branched homo-or heterooligomers thereof, other aliphatic and/or aromatic amino acids as well as linear and branched homo- or heterooligomers; amino-oligoalkoxyalkylamines; maleinimidocarb-oxylic acid derivatives; oligomers of alkylamines; 4-alkylphenyl derivatives; 4-oligoalkoxyphenyl or 4-oligoalkoxyphenoxy derivatives; 4-oligoalkyl-mercaptophenyl or 4-oligoalkylmercaptophenoxy derivatives; 4-oligoalkylaminophenyl or 4-oligoalkylaminophenoxy derivatives; (oligoalkylbenzyl)-phenyl or 4-(oligoalkylbenzyl)phenoxy derivatives, as well as 4-(oligoalkoxybenzyl)phenyl or 4-(oligoalkoxy-benzyl)phenoxy derivatives; trityl derivatives; benzyloxyaryl or benzyloxyalkyl derivatives; xanthen-3-yloxyalkyl derivatives; (4-alkylphenyl)- or ω-(4-alkylphenoxy)alkanoic acid derivatives; oligoalkylphenoxyalkyl or oligoalkoxyphenoxyalkyl derivatives; carbamate derivatives; amines; trialkylsilyl or dialkyialkoxysilyl derivatives; alkyl or aryl derivatives and/or combinations thereof.

In yet another embodiment the peptide according to the invention is characterized in that it is selected from the group consisting of:
a) a peptide consisting of the amino acid sequence

X1-X2-X3-X4-X5-X6-X7-X8-X9 wherein X1 to X9 have the same meaning as mentioned hereinabove;
b) a peptide consisting of an amino acid sequence having sufficient homology to be functionally analogous to an amino acid sequence in accordance with a);
c) a peptide according to an amino acid sequence a) or b) which is modified by deletions, additions, substitutions, translocations, inversions and/or insertions and functionally analogous to an amino acid sequence in accordance with a) or b);
d) a peptide according to amino acid sequence a), b) or c) which is modified by branch or extension with the same or another peptide according to amino acid sequence a), b) or c) to form a homooligomeric or heterooligomeric peptide.
e)

In a still further embodiment the peptide of the invention is characterized in that the amino acid sequence specified under b) has at least 40% homology to any of the amino acid sequences specified under a). Moreover, the peptide of the invention is characterized in that the amino acid sequence specified under b) has at least 60%, preferably 70%, more preferably 80%, especially preferably 90% homology to any of the amino acid sequences specified under a).

In yet another embodiment of the invention the peptide of the invention is characterized in that it consists of the amino acid sequence APEDET; (SEQ ID NO: 1) WKEPAP; (SEQ ID NO: 2); PPDERF (SEQ ID NO: 3); KMWTFG (SEQ ID NO: 4) or FGNFWCE (SEQ ID NO: 5).

According to the invention the peptide of the invention can be used as a medical active substance. The peptide according to the invention is able to bind to antibodies of patients suffering from Morbus Alzheimer.

The peptide of the invention is furthermore characterized in that it may be immobilized and/or fixed to magnetic, paramagnetic and/or non magnetic nanoparticles.

In still another embodiment of the invention, the peptide according to the invention is characterized in that it is bound to a solid phase.

The peptide of the invention may be present in a linear and branched as well as cyclic form. The peptide ring closure is e. g. effected through disulfide bridging when two cysteines are present, or through amide cyclization, which is optionally effected through side chains, through the C to the N termini or through a combination of the latter.

The peptide according to the invention may be further characterized in that the immunoglobulins to which it binds are agAAB which interact with the human β2-AR and α-AR.

The peptide according to anyone of the foregoing claims, characterized in that it additionally comprises amino groups, amides, hydrazides, azides, carbamates, acetyl groups, biotin groups, markers, spacers and/or linkers.

Subject matter of the invention is also an isolated nucleic acid molecule comprising:
a) a nucleic acid molecule comprising a nucleotide sequence which encodes at least one peptide selected from the group consisting of peptides according to claim 1;
b) a nucleic acid molecule which is complementary to a nucleotide sequence in accordance with a);
c) a nucleic acid molecule which undergoes hybridization with a nucleotide sequence according to a) or b) under stringent conditions;
d) a nucleic acid molecule comprising a nucleotide sequence having sufficient homology to be functionally analogous to a nucleotide sequence according to a), b) or c);
e) a nucleic acid molecule which, as a consequence of the genetic code, is degenerated into a nucleotide sequence according to a) through d); and
f) a nucleic acid molecule according to a nucleotide sequence of a) through e) which is modified by deletions, additions, substitutions, translocations, inversions and/or insertions and functionally analogous to a nucleotide sequence according to a) through e).

The nucleic acid molecule according to the invention having the nucleotide sequence specified under d) comprises at least 40%, in particular at least 60%, preferably 70%, more preferably 80%, especially preferably 90% homology to any of the nucleotide sequences specified under a) through c).

The nucleic acid molecule of the invention is a genomic DNA, a cDNA and/or an RNA.

Subject matter of the present invention is also a vector comprising a nucleic acid molecule according to the invention.

Also a host cell is subject matter of the invention comprising the vector according to the invention.

Solid phases for affinity chromatography or solid-phase extraction are subject matter of the invention too, comprising organic, inorganic, synthetic polymers or mixed polymers, preferably cross-linked agarose, cellulose, silica gel, polyamide and polyvinyl alcohols, which are optionally chemically activated, with peptides according to the invention, immobilized on the surface of the solid phase e. g. by covalent bonding or by adsorption. In particular, the peptides can be covalently bound to the solid phase on position X1, X2, X3, X4, X5, X6, X7, X8 and/or X9. It may be advantageous that the peptides are distanced from the support surface by linkers or spacers.

Subject matter of the invention is also a device for removing immunoglobulins from immunoglobulin-containing samples on solid phases, wherein the device contains the solid phase of the invention. Means for the entry of immunoglobulin-containing samples can also be provided.

Another subject matter of the invention is a pharmaceutical composition comprising the nucleic acid molecule according to the invention, the vector according to the invention, the host cell according to the invention, the peptide according to the invention, and/or the solid phase according to the invention, optionally together with a pharmaceutically tolerable carrier substance.

Moreover, a kit comprising a nucleic acid molecule according to the invention, a vector according to the invention, a host cell according to the invention, a peptide according to the invention, a solid phase according to the invention and/or a pharmaceutical composition according to the invention, optionally together with instructions for combining the contents of the kit and/or providing a formulation.

Subject matter of the invention is also an apparatus for chromatography, comprising peptides according to the invention. In particular, the apparatus is characterized in that the peptides are bound to the solid phase of the invention.

The invention is also concerned with the use of the nucleic acid molecule of the invention, the vector according to the invention, the host cell according to the invention, the peptide according to the invention, the solid phase according to the invention, the pharmaceutical composition according to the invention, the kit according to the invention, the apparatus according to the invention in the prophylaxis, diagnosis, therapy of AD as well as in the production or screening of a drug for the treatment of neurodegenerative diseases, such as AD.

The invention discloses also a method of treatment of Morbus Alzheimer by binding and/or removal of autoantibodies by means of peptides according to the invention bound to a solid phase.

EXAMPLES, MATERIALS AND METHODS

Isolation and cultivation of neonatal heart cells were performed as described previously (Wallukat, G. and Wollenberger, A. 1987. Effects of the serum gammaglobulin fraction of patients with allergic asthma and dilated cardiomyopathy on chronotropic β-adrenoceptor function in cultured rat heart myocytes. Biomed. Biochim. Acta. 78:634-639)

Cell culture. Briefly, single cells were dissociated from the minced ventricles of Wistar rats (1-2 days old) with a 0.25% solution of crude trypsin and were cultured as monolayers with a density of 800 cells/mm2 in Halle SM 20-I medium equilibrated with humidified air. The medium contained 10% heat-inactivated FCS and 2 µmol/l fluorodeoxyuridine (Serva, Heidelberg, Germany) the latter to prevent proliferation of nonmuscle cells.

On the third or fourth days, the cells were incubated for 2 h in 2 ml fresh serum-containing medium. Seven to 10 selected cells or synchronously contracting cell clusters per flask were counted for 15 s. The change of the pulsation rate were expressed as beats per minute. This procedure was repeated twice in different cultures to yield results representing a total of up to 30 cells for each sample.

Immunoglobulin fractions, agonist and antagonist drugs, peptides etc. were added singly or cumulatively as indicated. The basal contraction rate of the spontaneously beating cardiomyocytes was 162±4 min.

Preparation of the immunoglobulin fraction. The immunoglobulin fraction was isolated from 1- to 2-ml serum samples by ammonium sulfate precipitation at a saturation of 40%. The precipitates were washed and dissolved in dialysis buffer (154 mmol/l NaCl, 10 mmol/l sodium phosphate; pH 7.2). The procedure of precipitating, washing, and dissolving was repeated twice.

Finally, the immunoglobulins were taken up in 1 ml PBS (pH 7.2) and dialyzed at 4° C. for 30 hours against 1 l of dialysis buffer. The buffer was changed five times during dialysis. For detection of autoantibodies, the immunoglobulin fractions were added at a dilution of 1:20 or 1:40 to the flasks.

After the dialysis, the IgG fractions feature a concentration of 10-15 mg/ml, a maximum of 10 µg/ml of which are specific receptor antibodies. 50 µl of this IgG solution are pre-incubated with the peptides with the following concentration of peptides: 5 µl of a buffered solution of 100 µg/ml per 50 µl IgG solution. This mixture is pre-incubated at room temperature for 30 minutes and subsequently filled into the cell culture vials, after the former nutrient solution has been removed by pipet. The amount of the medium is 2 ml. The final concentration therefore is of 0.5-0.75 mg/ml for the IgG and 0.5 µg for the peptides. If the molecular weight of the peptide (10 mer) is set with 1 KD and that of the IgG is set with 150 KD, there is an excess of agAAB.

For the neutralization experiments, synthetic peptides corresponding to the sequence of the three extracellular loops of the human β2 AR or α1A-AR was added in excess (0.5 µg in 50 µl) to 50 µl of the immunoglobulin fraction. The mixtures were shaken and incubated at room temperature for 1 h. The 100-µl samples were then added to neonatal rat heart muscle cells cultured in 2 ml medium to a final dilution of 1:40. The beating rate was counted for 15 s, about 60 min after the addition of the peptide/immunoglobulin mixture.

For identifying the autoantibody neutralizing epitopes synthetic overlapping peptides corresponding to the sequence of the first extracellular loop of the human β2-AR or second extracellular loop of α1A-AR was added to the immunoglobulins. After 1 h incubation at room temperature the samples were used as described above.

ED50 calculation. For the estimation of the 50% effective dosage of agAAB to stimulate neonatale rat cardiomyocytes the affinity chromatographic purified antibodies which bind to the epitopes in loopl of the human β2 adrenoceptor or loop2 of the human α1 adrenocepotor (sub type A) the antibodies were given into the tissue culture containing neonatal rat cardiomyocytes sequencially with increasing of antibody concentration until the maximum of the increase of the beating rate was observed. The ED50 was calculated by a computer program.

Patients. Sera of 14 patients with dementia of the Alzheimer type were recruited from the Clinic of Psychiatry of the Hospital Luedenscheid. The controls are immunoglobulin fraction from the blood serum of healthy donors from the Max Delbrück Centre of Moleculare Medicine, Berlin.

For immunoglobulin preparation, the samples were centrifuged at 4,000 g for 30 min and stored at −20° C. Reagents was purchased from Sigma-Aldrich Chemie (Deisenhofen, Germany). All other chemicals were of analytical grade.

RESULTS

The figures show the following.

The β2 adrenergic antagonist ICI 118,551 blocks specifically but partially the stimulating effects of the agonistic antibodies. A more effective inhibition of cellular activity of contraction is observed if additional the α adrenergic antagonist prazosin was given into the cell culture. 11 from 14 serum samples or immunoglobulins activate the cardiac myocytes.

---

SEQUENCE LISTING

Figure 1:
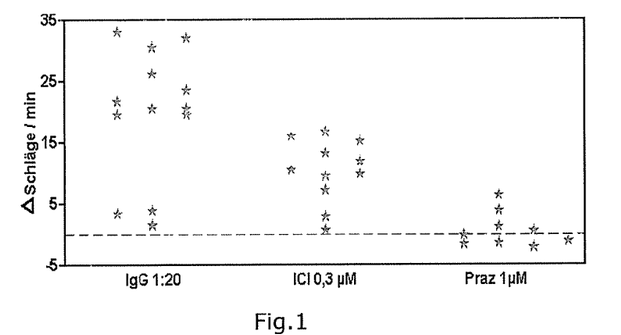
FIG. 1: Antibodies of patients (n=11-14) with Morbus Alzheimer stimulate rat cardiomyocytes via β2 adrenergic receptor and α1 adrenergic receptor.
Figure 2:
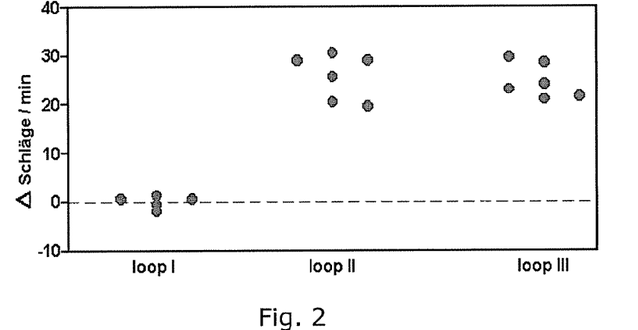
FIG. 2: Antibodies from patients (n=6) with Morbus Alzheimer bind to the first extracellular loop of the β2 Adrenoceptor. After coincubation of the extracellular loop peptides 1, 2 or 3 with the immunoglobulins of the patients only the loop 1 neutralise the antibody mediated increase of the cellular beating rate.
Figure 3:
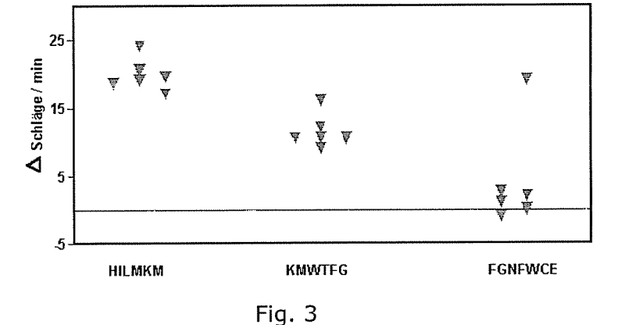
FIG. 3: Antibodies from patients (n=6) with Morbus Alzheimer bind to a peptide epitope embedded in the first extracellular loop of the β2-AR. After co-incubation of the immunoglobulins with overlapping epitopes (2 amino acids) of the loop 1 peptides a neutralisation of antibody mediated increase of the beating rate was observed with the epitope FGNFWCE (SEQ ID NO: 5).
Figure 4:
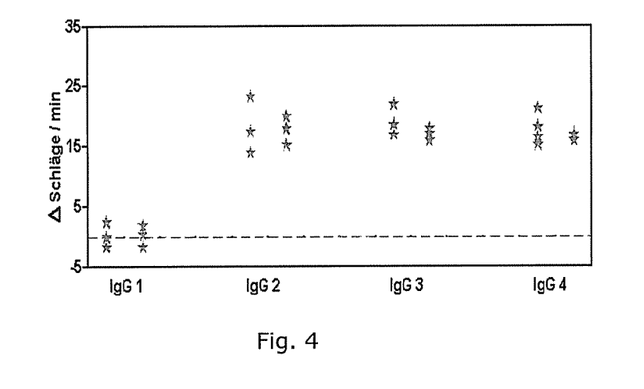
FIG. 4: Antibodies of patients (n=6) with Morbus Alzheimer and directed to the β2 Adrenoceptor belong to the immunoglobulin G subclass 1. After co-incubation of the immunoglobulins with monoclonal antibodies specific for the subclasses 1-4 only with the precipitate performed with the monoclonal antibody against IgG1 the antibody mediated activity disappeared.
Figure 5:
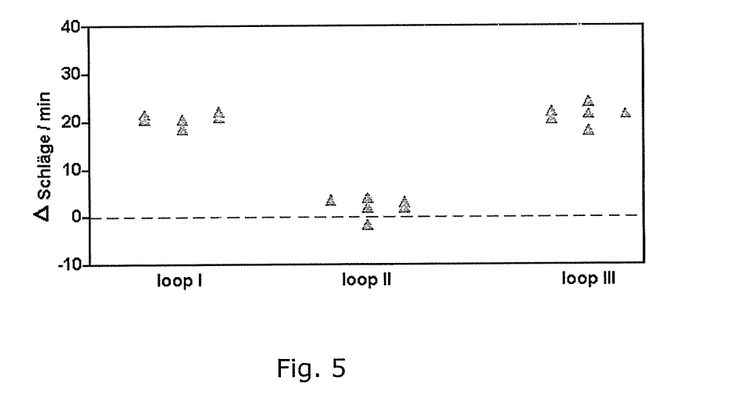
FIG. 5: Antibodies from patients (n=6) with Morbus Alzheimer bind to the second extracellular loop of the α1 Adrenoceptor. After co-incubation of the loops 1, 2 or 3 with the immunoglobulins of the patients only the loop 2 neutralise the antibody mediated increase of the cellular beating rate.
Figure 6:
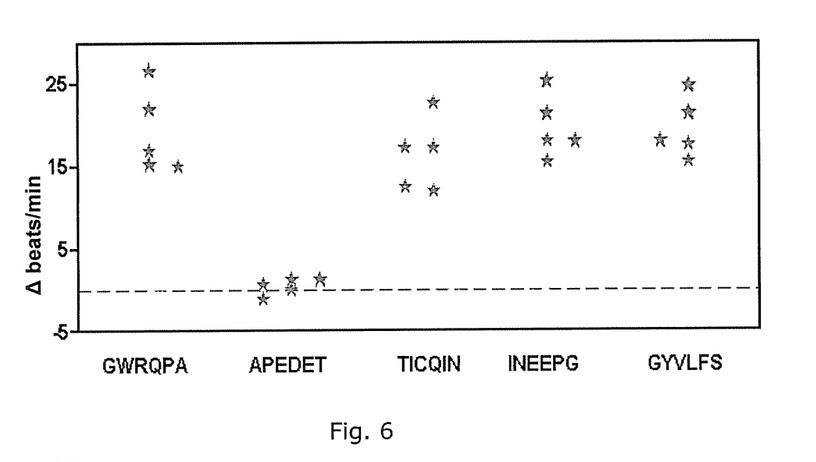
FIG. 6: Antibodies from patients (n=5) with Morbus Alzheimer are neutralized by a peptide embedded in the second extracellular loop of the α1A Adrenoceptor. Overlapping peptids (one or two aminoacids) were co-incubated with the immunoglobulins. The peptide with the amino acid sequence APEDET (SEQ NO:1) neutralises the cellular activity of the immunoglobulins.
Figure 7:
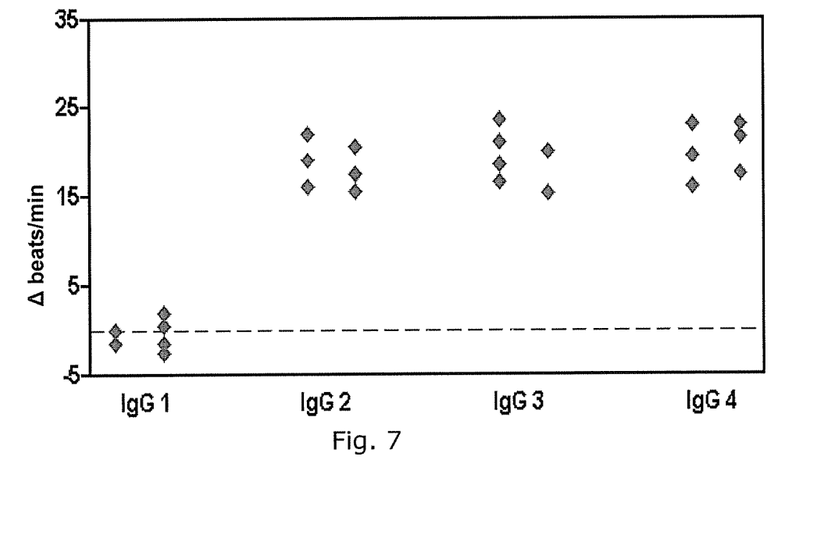
FIG. 7: Antibodies of patients (n=5) with Morbus Alzheimer and directed to the α1A Adrenoceptor belong to the immunoglobulin G subclass 1. After co-incubation of the immunoglobulins with monoclonal antibodies specific for the subclasses 1-4 only with the precipitate performed with the monoclonal antibody against IgG1 the antibody mediated activity disappeared.

```
<160> NUMBER OF SEQ ID NOS: 6

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Ala Pro Glu Asp Glu Thr
1               5

<210> SEQ ID NO 2
<211> LENGTH: 6
<212> TYPE: PRT
<213> ORGANISM: Artificial
<220> FEATURE:
<223> OTHER INFORMATION: synthetic peptide

<400> SEQUENCE: 2

Trp Lys Glu Pro Ala Pro
1               5

<210> SEQ ID NO 3
<211> LENGTH: 6
<212> TYPE: PRT
<213> ORGANISM: Artificial
<220> FEATURE:
<223> OTHER INFORMATION: synthetic peptide

<400> SEQUENCE: 3

Pro Pro Asp Glu Arg Phe
1               5

<210> SEQ ID NO 4
<211> LENGTH: 6
<212> TYPE: PRT
```

```
<213> ORGANISM: Artificial
<220> FEATURE:
<223> OTHER INFORMATION: synthetic peptide

<400> SEQUENCE: 4

Lys Met Trp Thr Phe Gly
1               5

<210> SEQ ID NO 5
<211> LENGTH: 7
<212> TYPE: PRT
<213> ORGANISM: Artificial
<220> FEATURE:
<223> OTHER INFORMATION: synthetic peptide

<400> SEQUENCE: 5

Phe Gly Asn Phe Trp Cys Glu
1               5

<210> SEQ ID NO 6
<211> LENGTH: 4
<212> TYPE: PRT
<213> ORGANISM: Artificial Sequence
<220> FEATURE:
<223> OTHER INFORMATION: peptide end segment

<400> SEQUENCE: 6

Ser Gly Lys Lys
1
```

The invention claimed is:

1. A peptide consisting of an amino acid sequence having at least 70% homology to the amino acid sequence     X1-FGNFWCE-X9    (SEQ ID NO: 5), wherein:
X1=amino group, amide, acetyl group, biotin group, spacer, linker, C, GKK, SGKK (SEQ ID NO: 6) or deletion; and
X9=amide, hydrazide, azide, carbamate, spacer, linker, C, GKK, SGKK (SEQ ID NO: 6) or deletion.

2. The peptide according to claim 1, characterized in that the peptide is immobilized and/or fixed to magnetic, paramagnetic and/or non magnetic nanoparticles.

3. The peptide according to claim 1, characterized in that the peptide is bound to a solid phase.

4. A pharmaceutical composition comprising the peptide of claim 1 in combination with a pharmaceutically tolerable carrier.

5. A kit comprising the peptide of claim 1, or a solid phase on which the peptide is immobilized, together with instructions for combining contents of the kit and/or providing a formulation.

6. The peptide of claim 1 consisting of an amino acid sequence having at least 80% homology to the amino acid sequence X1-FGNFWCE-X9 (SEQ ID NO: 5).

7. The peptide of claim 1 consisting of an amino acid sequence having at least 90% homology to the amino acid sequence X1-FGNFWCE-X9 (SEQ ID NO: 5).

* * * * *